(12) United States Patent
Goldman et al.

(10) Patent No.: US 9,517,163 B2
(45) Date of Patent: Dec. 13, 2016

(54) PRE-STRESSED PRESSURE DEVICE

(71) Applicant: 3K Anesthesia Innovations LLP, Redding, CT (US)

(72) Inventors: Boris Goldman, Newtown, CT (US); Eric Kitain, Armonk, NY (US); Robert Koorn, Redding, CT (US); Vladimir Koltchine, Redding, CT (US)

(73) Assignee: 3K ANESTHESIA INNOVATIONS, LLP, Redding, CT (US)

( * ) Notice: Subject to any disclaimer, the term of this patent is extended or adjusted under 35 U.S.C. 154(b) by 176 days.

(21) Appl. No.: 13/934,600

(22) Filed: Jul. 3, 2013

(65) Prior Publication Data

US 2015/0012037 A1    Jan. 8, 2015

(51) Int. Cl.
| | |
|---|---|
| A61B 17/08 | (2006.01) |
| A61F 13/02 | (2006.01) |
| A61B 17/132 | (2006.01) |
| A61F 13/00 | (2006.01) |
| A61B 17/00 | (2006.01) |

(52) U.S. Cl.
CPC .......... *A61F 13/02* (2013.01); *A61B 17/1325* (2013.01); *A61F 13/00063* (2013.01); *A61F 13/025* (2013.01); *A61F 13/0206* (2013.01); *A61B 2017/00526* (2013.01); *A61F 2013/0028* (2013.01); *A61F 2013/00217* (2013.01)

(58) Field of Classification Search
CPC ................. A61B 17/1325; A61B 2017/00526; A61B 13/02; A61F 2013/0028; A61F 5/00; A61F 13/02; A61F 2013/00468; A61F 13/0236; A61F 13/0263; A61F 13/0266; A61F 13/0203

USPC ...................... 602/41–59; 606/201, 213–215
See application file for complete search history.

(56) References Cited

U.S. PATENT DOCUMENTS 4,377,159 A     3/1983 Hansen
5,170,781 A *  12/1992 Loomis ...................... 128/118.1
(Continued)

FOREIGN PATENT DOCUMENTS

| CN | 201101634 Y | 8/2008 |
| CN | 202184763 U | 4/2012 |
(Continued)

OTHER PUBLICATIONS

International Search Report and the Written Opinion of the International Searching Authority dated Sep. 19, 2014 from the corresponding International Application No. PCT/US2014/044244.
(Continued)

*Primary Examiner* — Kari Petrik
(74) *Attorney, Agent, or Firm* — Welsh Flaxman & Gitler LLC

(57) ABSTRACT

A pre-stressed pressure device for treating a wound or reduce scarring of a skin of a patient includes a substrate assembly having a first surface, a pressure member having a curve in a central portion, the pressure member being secured to the substrate assembly; a treatment device for exerting a pressure on the wound or the scarring, the treatment device being connected to a first area of the first surface; and an adhesive for applying the pressure bandage to the skin, the adhesive being disposed on a second area of the first surface, the first and second areas being non-overlapping.

4 Claims, 9 Drawing Sheets

(56) References Cited

U.S. PATENT DOCUMENTS

| | | | |
|---|---|---|---|
| 5,209,718 A * | 5/1993 | McDaniel | A61F 13/0203 128/109.1 |
| 5,376,067 A | 12/1994 | Daneshvar | |
| 5,512,056 A * | 4/1996 | Stevens et al. | 606/203 |
| 5,690,610 A * | 11/1997 | Ito | A61F 13/0203 602/46 |
| 5,891,074 A | 4/1999 | Cesarezyk | |
| 5,939,339 A | 8/1999 | Delmore et al. | |
| 6,573,419 B2 | 6/2003 | Naimer | |
| 6,812,375 B2 | 11/2004 | Dennis et al. | |
| 8,034,009 B2 | 10/2011 | Bates et al. | |
| 8,063,263 B2 | 11/2011 | Gurtner et al. | |
| 8,163,973 B2 | 4/2012 | Johnson | |
| 8,409,156 B2 | 4/2013 | Kazala, Jr. et al. | |
| 8,591,493 B2 | 11/2013 | McGuire, Jr. | |
| 2005/0095276 A1 | 5/2005 | Kartheus et al. | |
| 2006/0211976 A1 | 9/2006 | Ramsey | |
| 2007/0260165 A1 | 11/2007 | Johnson | |
| 2008/0234754 A1 | 9/2008 | McCarthy et al. | |
| 2009/0099496 A1 | 4/2009 | Heegaard et al. | |
| 2009/0131846 A1 | 5/2009 | Gurtner et al. | |
| 2012/0046586 A1 | 2/2012 | Gurtner et al. | |
| 2012/0226214 A1 | 9/2012 | Gurtner et al. | |
| 2012/0226306 A1 | 9/2012 | Jackson et al. | |

FOREIGN PATENT DOCUMENTS

| | | |
|---|---|---|
| WO | 03/080133 | 10/2003 |
| WO | 2007044647 | 4/2007 |
| WO | 2008089172 | 7/2008 |

OTHER PUBLICATIONS

Geoffrey C. Gurtner, MD, et al: "Improving Cutaneous Scar by Controlling the Mechanical Environment", Nov. 2011, ISSN: 0003-4932/11/00000-0001, DOI: 10.1097/SLA.0b013e318220b159.

Michael T. Longaker, M.D., et al: The embrace Device Significantly Decreases Scarring following Scar Revision Surgery in a Randomized Controlled Trial, Jul. 12, 2013, DOI: 10.1097/01.prs.00004436526.64046.d0.

Website plasticsurgery.about.com/b/2011/06/09/scars-after-plastic-surgery-a-thing-of-the-past.htm (2 pages) retrieved Jun. 26, 2013.

\* cited by examiner

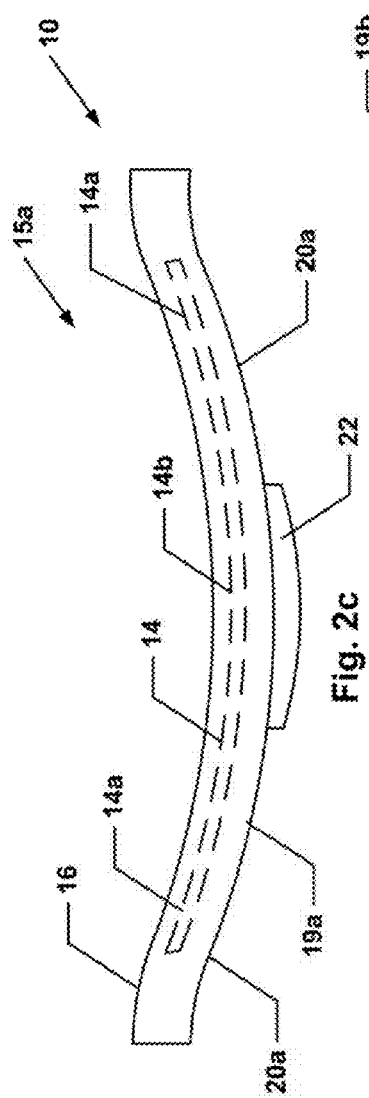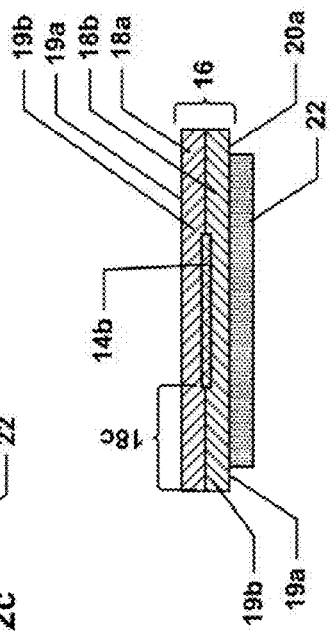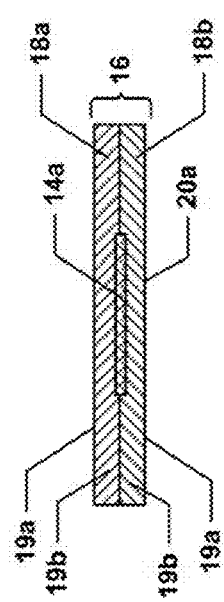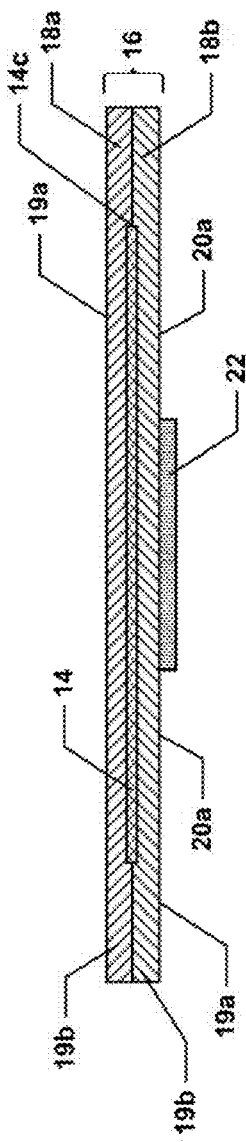

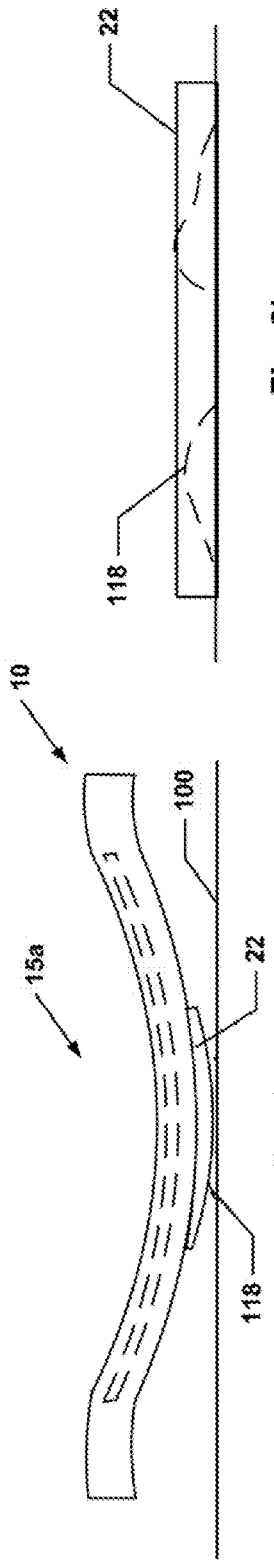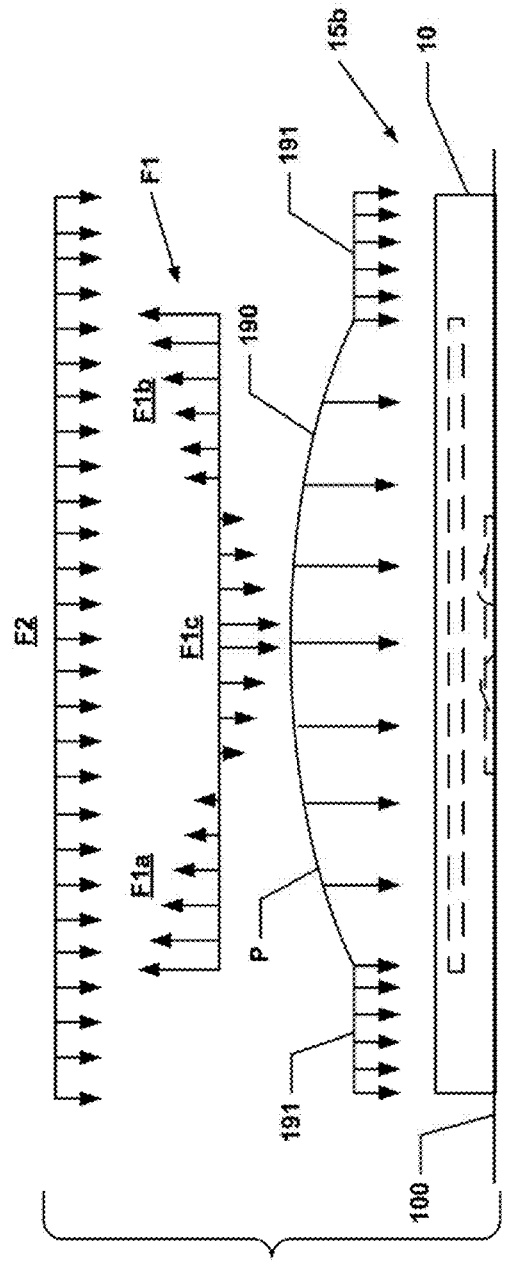

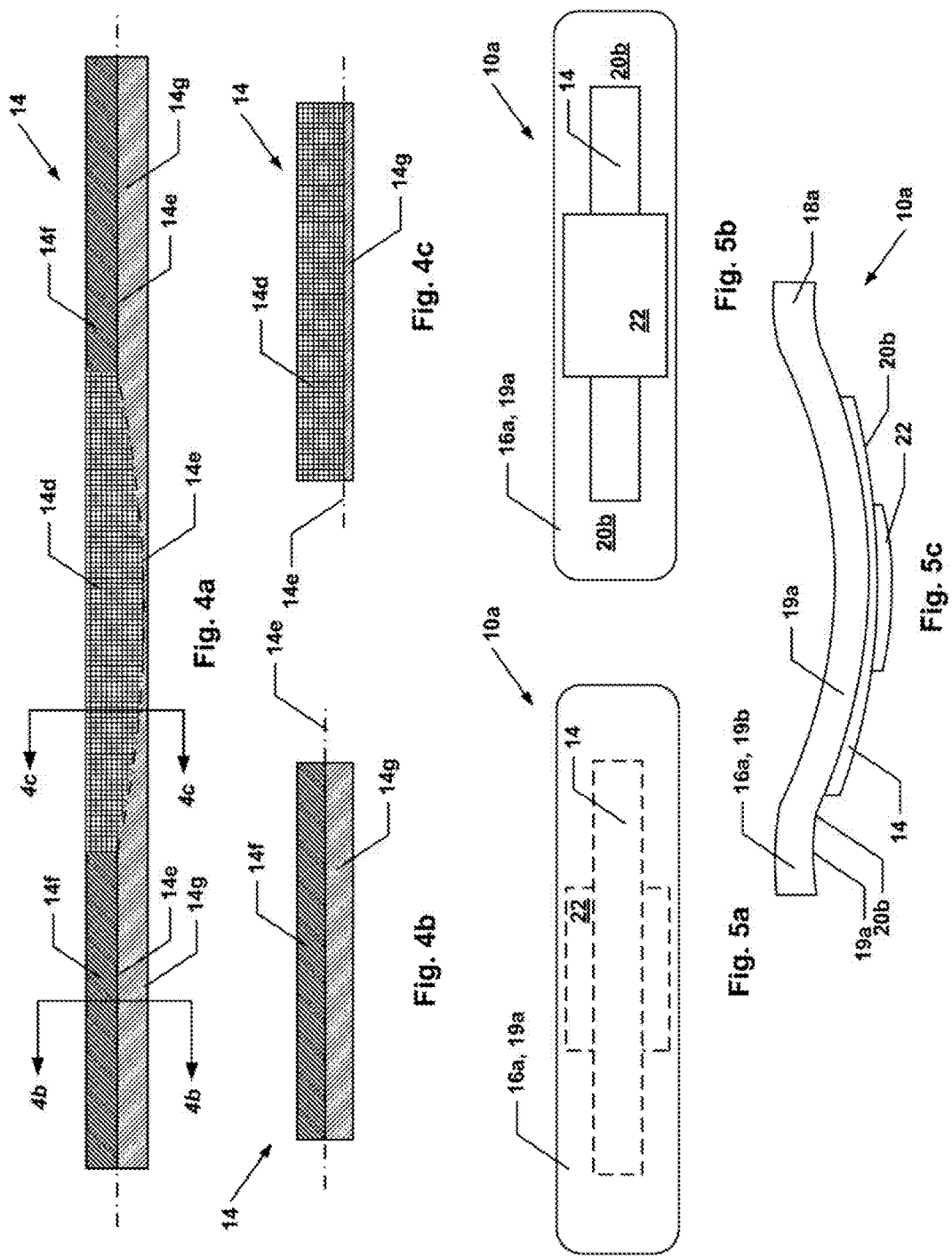

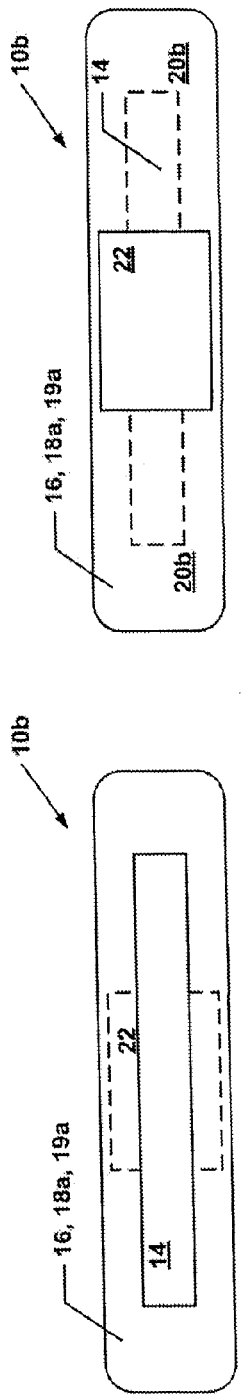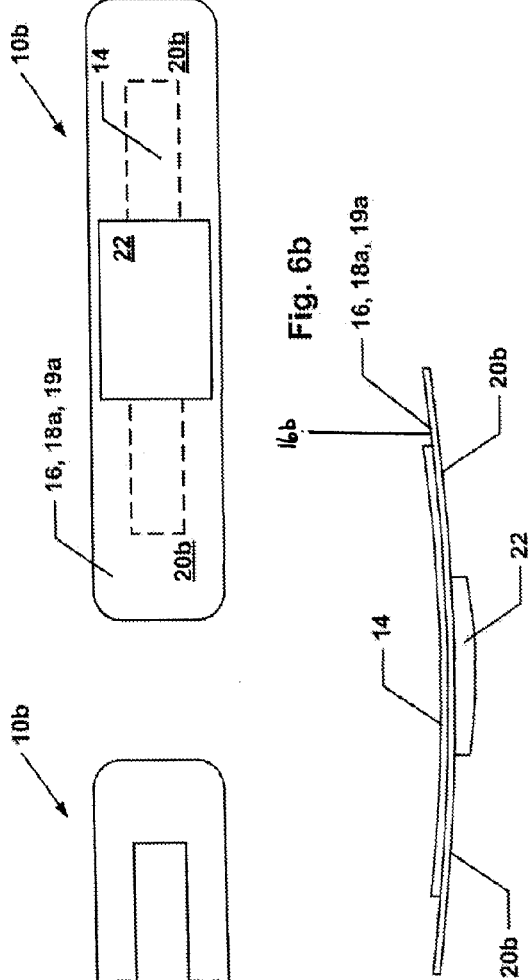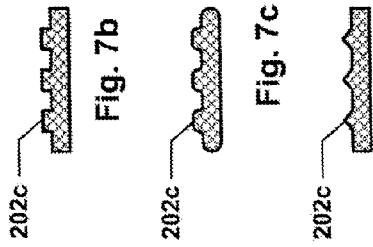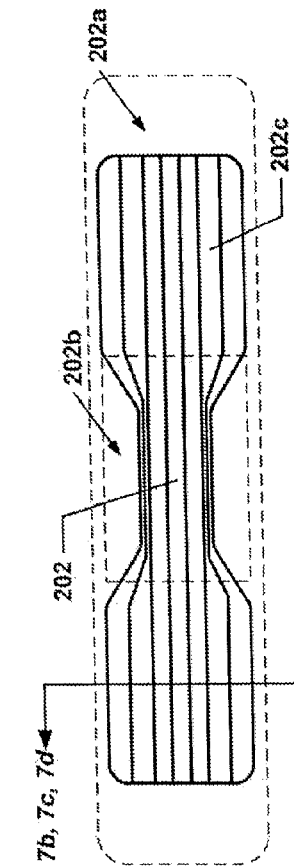

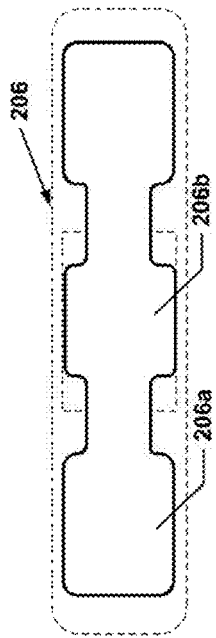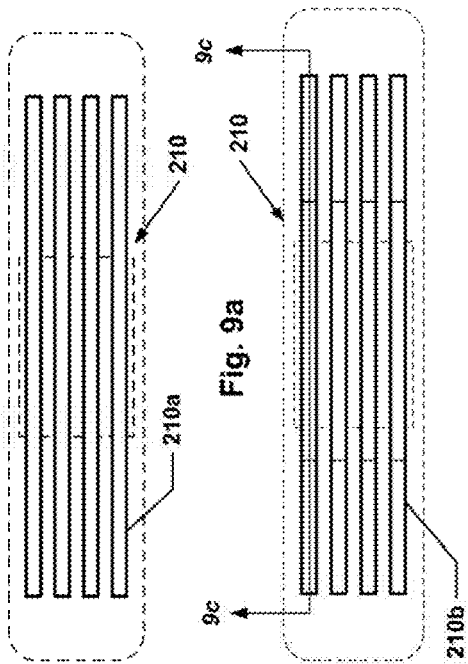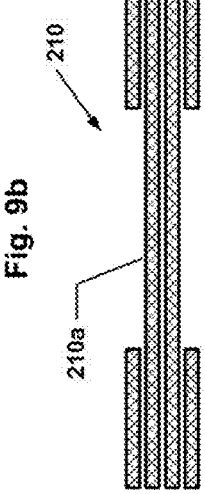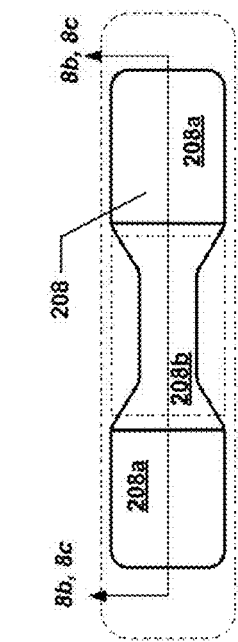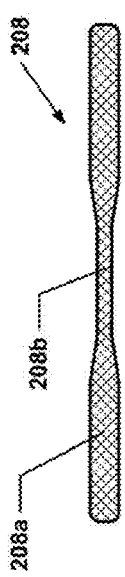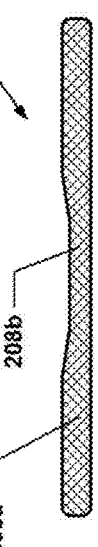

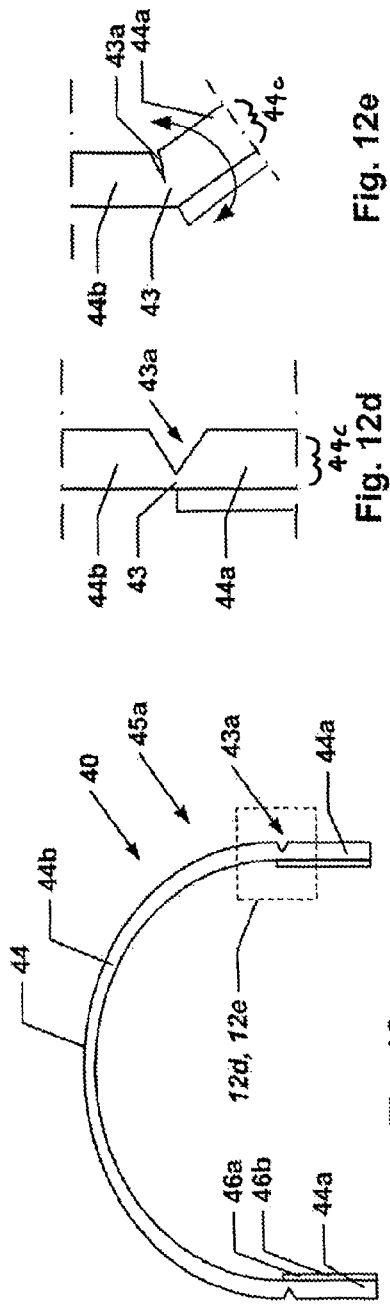
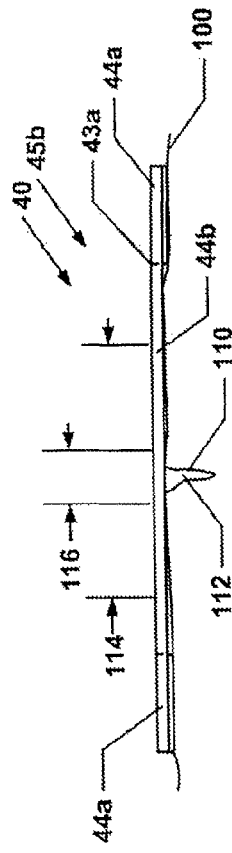
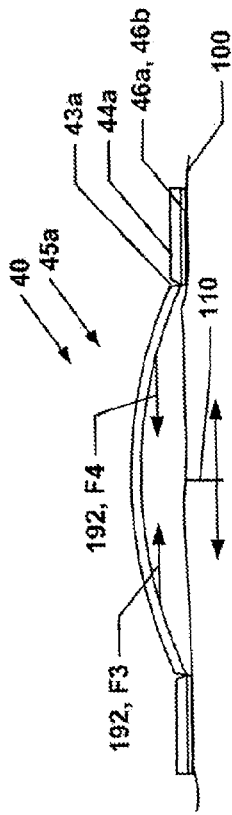

PRE-STRESSED PRESSURE DEVICE

BACKGROUND OF THE INVENTION

1. Field of the Invention

The invention relates to a device and system for treating a patient. Specifically, the invention relates to a pre-stressed pressure device that applies pressure to a wound and/or scar to promote healing and reduce the appearance of scars and to a system for making and using the pre-stressed pressure device.

2. Description of the Related Art

Applying pressure to a patient's wound is beneficial because pressure provides immediate hemostasis and decreases swelling and bruising associated with the wound. An added benefit for traumatic or surgical wounds that require sutures is diminished swelling resulting in less tension across the suture lines. This facilitates healing and improves the quality of the final scar by decreasing suture marks and irregularities formed in the skin as the tissue surrounding the wound heals.

Wounds may take many forms. Herein, "wound" is intended to be as broadly inclusive as possible and means one or more injuries to at least the skin of a person. Wound may mean cuts and lacerations that are self-treated by a patient. It may also mean serious wounds caused by traumatic injuries that are treated in a medical setting; wounds caused by surgery; or vascular cutaneous puncture sites such as intravenous catheter, arterial catheter, or the like.

As wounds heal, applying pressure prevents scarring. The skin at any site of the body comprises an intrinsic tension that stretches the marginal area of the skin surrounding the wound. The actual amount of tension may vary, depending upon the person, age, skin type, and wound location. Pre-existing skin conditions, such as scarring, may also affect the intrinsic tension. During the intermediate phase of a wound healing process (between 2 weeks and 12 weeks), the edges of a healing incision or wound, are pulled in different directions by surrounding skin, causing formation of the scar tissue.

Even after scarring has formed, applying pressure is an integral component of a scar reduction regimen. Typically, a silicone gel sheet is fastened to a patient using a bandage wrapped tightly around the patient's limb or torso. When combined with glucocorticoid steroids, the result reduces the appearance of hypertrophic (thick) scars.

Herein, "scar" and/or "scarring" is intended to be as broadly inclusive as possible and means at last one or more temporary or permanent deformations of any part of the skin due to injury to the skin.

Unfortunately, to date, the various technologies available for providing pressure on a wound and/or scar require bulky or impractical devices. Thus, what is desired is a wound and scar treatment that provides pressure to a wound and/or scar and that is compact and a system for making and using that treatment.

SUMMARY OF THE INVENTION

These and other objectives are met by the present invention.

In accordance with one or more embodiments of the present invention, a pre-stressed pressure device is preferably configured as a pressure bandage for treating a wound or to reduce scarring of the skin of a patient. The pressure bandage includes a substrate assembly having a first surface, a pressure member having a curve in a central portion, the pressure member being secured to the substrate assembly; a treatment device for exerting a pressure on the wound or the scarring, the treatment device being connected to a first area of the first surface; and an adhesive for applying the pressure bandage to the skin, the adhesive being disposed on a second area of the first surface, the first and second areas being non-overlapping.

In accordance with one or more embodiments of the present invention, a pre-stressed pressure device is preferably configured as a pressure bandage for treating a patient. The pressure bandage includes a substrate assembly, a treatment device mounted on the substrate assembly, an adhesive disposed on the substrate assembly, the adhesive for securing the pressure bandage to the patient, and a pressure member secured to the substrate assembly. Therein, the pressure member is in a substantially curved state when the pressure bandage is not secured to the patient.

The pressure member includes a center portion and an end portion, which have a different thickness or a different width from each other.

The pressure member includes a plurality of disconnected portions disposed in a plurality of planes.

A system for treating a wound or scarring of a patient includes a pressure bandage comprising a pressure member having a pre-tension, a 3D printer for printing the pressure member, and a heater for selective heating an area of the pressure member to impart the pre-tension.

BRIEF DESCRIPTION OF THE DRAWINGS

FIG. 2b is a bottom plan view of the bandage of FIG. 2a.

FIG. 2c is a longitudinal side view of the bandage of FIG. 2b.

FIG. 2d is a first transverse cross-sectional view of the bandage of FIG. 2a.

FIG. 2e is a second transverse cross-sectional view of the bandage of FIG. 2a.

FIG. 2f is a longitudinal cross-sectional view of the bandage of FIG. 2a.

FIG. 3a is a schematic view of the bandage of the present invention of FIG. 2a prior to being applied to the wound of FIGS. 1a and 1b.

FIG. 3b is a detail view of the treatment device of the present invention of FIG. 2a after being applied to the wound of FIGS. 1a and 1b.

FIG. 3c is a schematic view of the present invention of FIG. 2a after being applied to the wound of FIGS. 1a and 1b and pressure diagrams associated with the present invention.

FIG. 4a is a longitudinal cross-sectional view of the pressure member of the bandage of FIG. 2a.

FIG. 4b is a first transverse cross-sectional view of the pressure member of FIG. 4a.

FIG. 4c is a second transverse cross-sectional view of the pressure member of FIG. 4a.

FIG. 5a is a top plan view of a bandage in accordance with one or more embodiments of the present invention.

FIG. 5b is a bottom plan view of the bandage of FIG. 5a.

FIG. 5c is a longitudinal side view of the bandage of FIG. 5b.

FIG. 6a is a top plan view of a bandage in accordance with one or more embodiments of the present invention.

FIG. 6b is a bottom plan view of the bandage of FIG. 6a.

FIG. 6c is a longitudinal side view of the bandage of FIG. 6b.

FIG. 7a is a plan view of a pressure member in accordance with one or more embodiments of the present invention.

FIG. 7b is a cross-sectional view of the pressure member of FIG. 7a.

FIG. 7c is a first alternate cross-sectional view of the pressure member of FIG. 7a.

FIG. 7d is a second alternate cross-sectional view of the pressure member of FIG. 7a.

FIG. 7e is a plan view of a pressure member in accordance with one or more embodiments of the present invention.

FIG. 7f is a plan view of a pressure member in accordance with one or more embodiments of the present invention.

FIG. 8a is a plan view of a pressure member in accordance with one or more embodiments of the present invention.

FIG. 8b is a longitudinal cross-sectional view of the pressure member of FIG. 8a.

FIG. 8c is an alternate longitudinal cross-sectional view of the pressure member of FIG. 8a.

FIG. 9a is a plan view of a pressure member in accordance with one or more embodiments of the present invention.

FIG. 9b is a plan view of a pressure member in accordance with one or more embodiments of the present invention.

FIG. 9c is a longitudinal cross-sectional view of the pressure member of FIG. 9b.

FIG. 12a is a longitudinal side view of a pre-stressed pressure device that is configured as a stress guard prior to being applied to a patient in accordance with one or more embodiments of the present invention.

FIG. 12b is a longitudinal side view of the stress guard of FIG. 12a applied to a patient when initially applied to an open incision site.

FIG. 12c is a longitudinal side view of the stress guard of FIG. 12a after being stressed.

FIG. 12d is a first detail view of the stress guard of FIG. 12a.

FIG. 12e is a second detail view of the stress guard of FIG. 12a.

DETAILED DESCRIPTION OF THE INVENTION

Figure 1A:
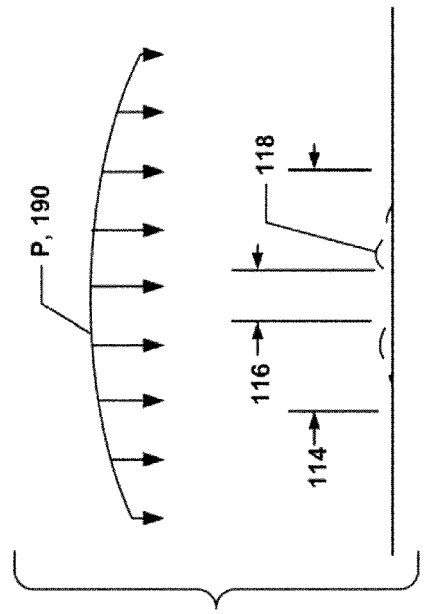
FIG. 1a is a schematic plan view of a wound and scar being treated by the present invention.

The following detailed description is of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention. In the various views of the drawings, like reference characters designate like or similar parts.

Figure 1B:
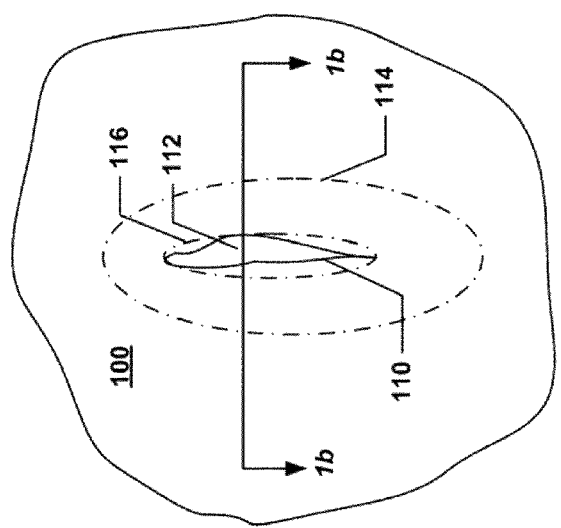
FIG. 1b is a cross-sectional area view of the wound of FIG. 1a being treated by the present invention and a pressure diagram associated with the present invention.

FIG. 1a is a schematic plan of a wound and scar being treated by the present invention. FIG. 1b is a cross-sectional area of the wound of FIG. 1a being treated by the present invention and a pressure diagram associated with the present invention.

Therein, a patient 100 has sustained a wound 110 as is commonly understood and at least as defined in the Description of the Related Art. The wound 110 has a wound area 112 that is determined by the type and cause of the wound and a treatment area 114. The treatment area extends from a regularized margin 116 of the wound to encompass the wound and an area most likely to be scarred by scarring 118, such as hypertrophic, as determined by a patient, but preferably by a qualified medical practitioner. A "regularized margin" herein means a theoretical margin of the wound that extends in a regular geometric pattern of an ellipse or a circle about the wound and touches the furthest extent of the actual margin of the wound at at least three points. To treat the wound 110 and prevent likely scarring 118, a pressure P, shown as exemplary pressure 190 in the pressure diagram of FIG. 1b, is applied by a treatment device (not shown) on at least the treatment area 114 using a pressure bandage 10.

It should be understood that the present invention may also be applied to only a scar. Therein, the wound area 112 is nil and the treatment area 114 extends to encompass the area scarred by scarring 118, such as hypertrophic scarring, as determined by a patient, but preferably by a qualified medical practitioner. To treat scarring 118, pressure P, is applied by a treatment device on at least the treatment area 114 using a pressure bandage 10.

Pressure P is preferably non-uniform and is greater over the treatment area 114 than in other areas where the pressure bandage is applied. The particular diagrammatic shape and/or amount of pressure P are dependent on the shape of a pressure member in plan view, thickness, and amount, i.e., degree of pre-stressing.

Figure 2B:
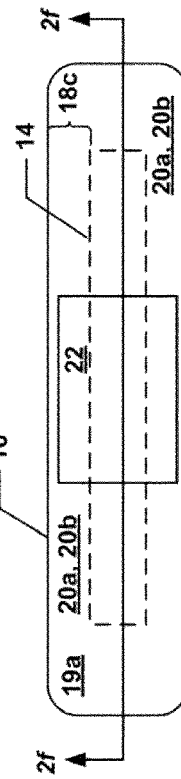
Figure 2A:
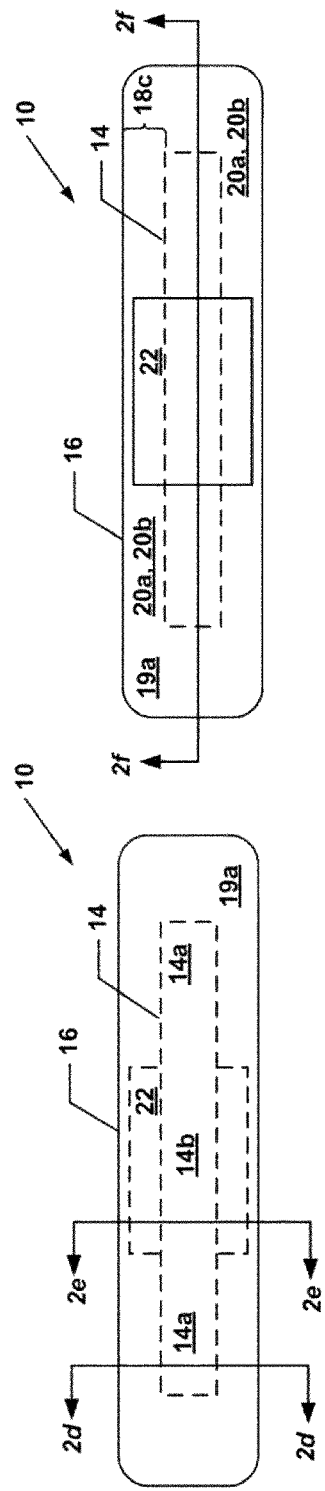
FIG. 2a is a top plan view of a pre-stressed pressure device that is configured as a bandage in accordance with one or more embodiments of the present invention.
Figure 10C:
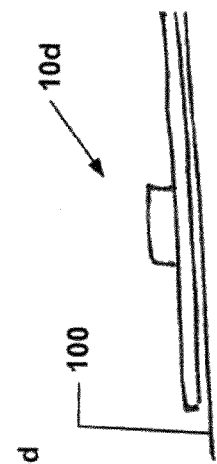
FIGS. 10a-10c and 11a-11c are, respectively, plan, side, and side on skin views of a bandage in accordance with one or more embodiments of the present invention.
Figure 11C:
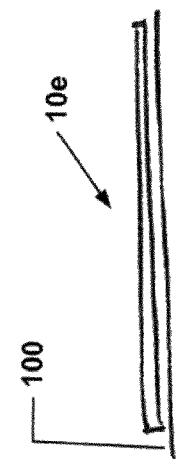
Figure 10B:
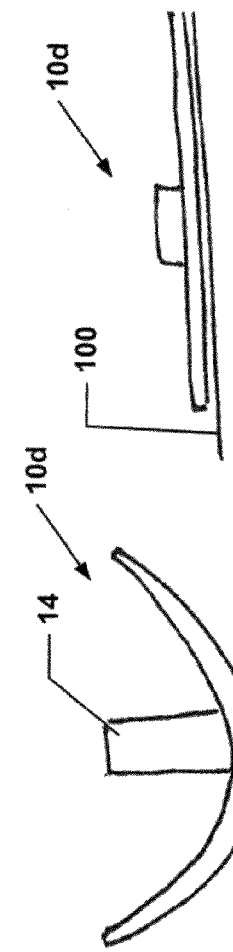
Figure 11B:
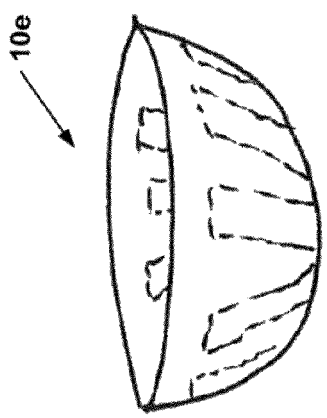
Figure 10A:
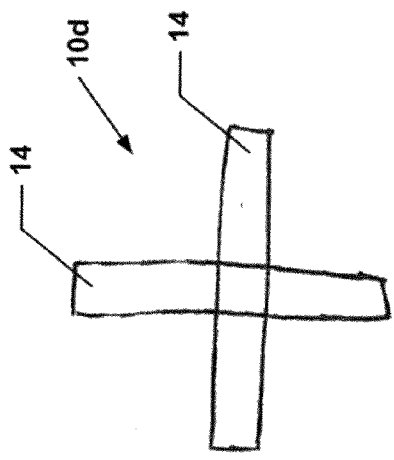
Figure 11A:
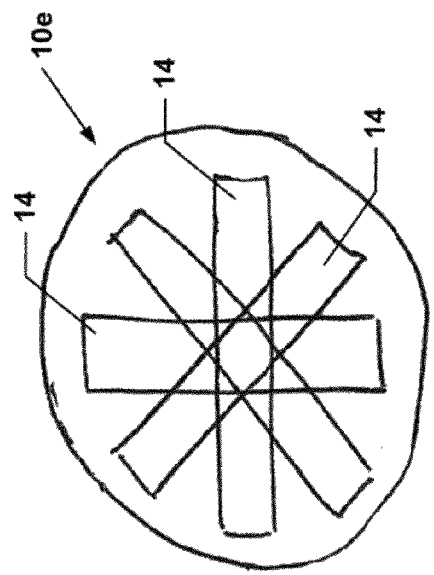

FIG. 2a is a top plan view of a pre-stressed pressure device that is configured as a bandage in accordance with one or more embodiments of the present invention. FIG. 2b is a bottom plan view of the bandage of FIG. 2a. FIG. 2c is a longitudinal side view of the bandage of FIG. 2b. FIG. 2d is a first transverse cross-sectional view of the bandage of FIG. 2a. FIG. 2e is a second transverse cross-sectional view of the bandage of FIG. 2a. FIG. 2f is a longitudinal cross-sectional view of the bandage of FIG. 2a.

FIG. 3a is a schematic view of the bandage of the present invention of FIG. 2a prior to being applied to the wound of FIGS. 1a and 1b. FIG. 3b is a detail view of the treatment device of the present invention of FIG. 2a after being applied to the wound of FIGS. 1a and 1b. FIG. 3c is a schematic view of the present invention of FIG. 2a after being applied to the wound of FIGS. 1a and 1b and pressure diagrams associated with the present invention.

FIG. 4a is a longitudinal cross-sectional view of the pressure member of the bandage of FIG. 2a. FIG. 4b is a first transverse cross-sectional view of the pressure member of FIG. 4a. FIG. 4c is a second transverse cross-sectional view of the pressure member of FIG. 4a.

In accordance with one or more embodiments of the present invention, a pre-stressed pressure device is configured as a pressure bandage 10. The pressure bandage 10 is preferably used for treating the wound 110 and comprises a pressure member 14, a substrate assembly 16, and a treatment device 22 joined to the substrate assembly. The pressure member 14 is secured to the substrate assembly 16 and applies a force to the treatment device 22. In turn, the treatment device 22 applies pressure P, i.e., the pressure 190, within at least the treatment area 114 of patient 100 to promote healing and/or reduce scarring when the bandage 10 is secured to the skin of the patient 100.

The pressure member 14 comprises one or more layers of one or more pressure materials. A pressure material may be any suitable material that is elastic and capable of holding an initial non-flat shape, preferably a curved shape. However, preferably, the pressure material is a polymer material. More preferably, the pressure material is selected from the group of polyvinyl chloride (PVC), acrylonitrile butadiene styrene (ABS); nylon polymers including polyamide 6, polyamide 66, homopolymers, and co-polymers; polyester resin; low-density polyethylene terephthalate (PET); low-density polyethylene, high-density polystyrene; high-density polyethylene; and rubberized and/or plasticized PVC.

The pressure member 14 comprises, but not necessarily, a generally rectangular shape in plan view having end portions 14a (each defined as being generally, but not necessarily, the one-third end area in plan view of the pressure member) spaced distal from a central portion 14b (defined as being generally, but not necessarily, the center one third area in plan view of the pressure member) and has a thickness 14c. The thickness 14c is preferably sufficient to prevent the longitudinal edges of the pressure member 14 from curling inwards towards the longitudinal centerline of the pressure member. That is, the thickness 14c is chosen such that the pressure member remains rigid in a cross-section perpendicular to the longitudinal centerline of the pressure member.

Therein, the thickness 14c may be varied as needed for the specific embodiment of the bandage 10 and may be non-uniform and variable in thickness across the width and/or along the length of the pressure member 14. The thickness preferably also provides the bandage 10 with sufficient load carrying capacity to achieve the desired pressure strains needed for the therapeutic effect on the wound 110 and/or the scarring 118. The thickness 14c of the pressure member 14 may be tapered near the edges for added comfort and/or safety of use.

The pressure member 14 normally has a curved shape in at least part of the central portion 14b while the end portions 14a are straight. In other words, the pressure member 14 has a normally curved state 15a, i.e., first state. This state occurs prior to the pressure bandage 10 being applied to the skin of the user.

The curved shape in at least part of the central portion 14b may be achieved by casting, extruding, and/or forming central portion to be curved. Therein, the central portion 14b may have any suitable curve while the end portions 14a are straight.

The curved shape may also be made by pre-stressing the pressure member in a pre-stressed area 14d (FIG. 4a), such as being heat-treated. Therein, the pre-stressed area 14d is preferably disposed in the central portion 14b. In the pre-stressed area, the pressure member has been stressed increasing the compression side 14e, moving the neutral axis 14f in the pre-stressed area 14d, and causing the tension side 14g to be reduced.

In the curved state 15a, the pressure member 14 is curved in the pre-stressed area 14d, i.e., at least part or all of the central portion 14b, while the end portions 14a are straight. Therein, the end portions 14a are preferably, but not necessarily, equidistant from the central portion 14b in lateral and offset directions and are curved in the same direction. When the pressure member 14 is in the curved state 15a, the bandage 10 generally follows the same curved contour as the pressure member 14 and also is in the curved state 15a.

When the bandage 10 has been applied to the patient 100, the pressure member 14 will be in a non-curved, substantially non-curved state 15b, i.e., second state. When the pressure member 14 is in substantially the non-curved state 15b, the bandage 10 generally follows the same contour as the pressure member 14 and also is in substantially the non-curved state 15b. The non-curved state 15b may be a flat state or contour, and/or may be one where the pressure member, i.e., pressure bandage, follows the contour of the skin.

In the substantially non-curved state 15b, the pressure member 14 exerts a force F1. The force F1 has end forces F1a and F1b directed away from the patient 100 and a central force F1c directed toward the patient 100 and forcing the treatment device 22 onto at least the treatment area 114. That is, when the pressure member 14 is straightened, the region of the pressure member 14 that has not been pre-stressed will pull upwards with forces F1a and F1b in an evenly dispersed manner while the force F1c in the region that has been pre-stressed, i.e., the central portion 14b, will be applied downward with a force equal to the sum of the forces F1a and F1b. The force F1c will be at maximum at the center the pressure member vary along the central portion 14b.

Advantageously, the pressure material may be pre-stressed to a predetermined amount, and thus, the amount of curvature may be selectively predetermined to the pressure member 14. In turn, by varying the curvature, the central portion 14b can be predetermined to exert a specific force F1c on the wound 110. In addition or in the alternative, the shape and/or the thickness 14c of the pressure member may be selected, as taught further herein, to provide further predetermined refinement of the force F1c. For example, by increasing the size of the edge portions 14a relative to the central portion 14b, a greater force F1c will be generated. The force F1c is transferred as pressure to the patient via the treatment device, since pressure is force per unit area.

Therein, increasing the force F1c will yield an increase in pressure applied to at least the treatment area 114 via the treatment device.

The pressure member 14 may have a thickness of 100 microns to at least 1 mm, but preferably with a range of about 220 microns to about 500 microns, or more preferably 300 microns to 400 microns.

The substrate assembly 16 comprises at least two substrate members 18a, 18b and an adhesive 20a applied in an adhesive area 20b of the substrate assembly 16. Substrate members 18a, 18b may be made of any suitable material 19a that is durable, stretchable, and resiliently flexible as is known in the art for adhesive bandages.

However, preferably, each substrate member, when made of a single layer, comprises or consists of a material 19a and, when made of a multilayer structure, comprises a covering made of a material 19a and one or more support layers made of a material 19b. The material 19a used may be made entirely of or comprise a woven material such as cloth in any suitable weave strength and may metal-detectable fabric, such as metal fibers, to permit the use of the bandage 10 in food service and/or processing industry. The material 19a may also be a light woven material for comfort or a heavy woven material for protection. The material may be chosen such that it is air permeable to permit air to access the wound 110 and/or the treatment area 114.

The material 19a may also be made entirely of or comprise a plastic material or rubber material as is known in the art for adhesive bandages due to their excellent stretchability, costs, and/or wearability.

The substrate members 18a and 18b may also comprise a multilayer structure. Therein, one or more material layers comprise or consist of a material 19b, which may be cotton, artificial and/or natural fibers, artificial and/or natural gel materials, natural or artificial foamed rubber and/or vinyl, or a combination thereof may be added to the covering.

The adhesive 20a may be one or more suitable pressure-sensitive adhesives as is known in the art for adhesive bandages. Due to their excellent adhesion strength, usability, costs, and/or length of use, the adhesive 20a is preferably selected from the group of acrylic, silicone, butyl rubber, nitrile, styrene block copolymers (SBC), ethylene-vinyl acetate (EVA), or a combination thereof. In addition or in the alternative, the adhesive 20a may be a polyacrylate-based, polyisobutylene-based, and/or silicone-based pressure-sensitive adhesive; or a synthetic rubber, acrylic, hydrocolloid, or a like compound adhesive. In addition or in the alternative, the adhesive 20a may also be a light-curable or heat-curable adhesive.

Preferably, regardless of type, the adhesive 20a comprises a T-peel release force of in the range of 0.45 N/cm to at least 19 N/cm. Therein, the T-peel release force and blunt probe tack force of pressure-sensitive adhesives is in accordance with ASTM D1876 and ASTM D2979 or other appropriate methods.

The adhesive 20a is applied in the adhesive area 20b to the substrate assembly. Therein, the adhesive area 20b is preferably a marginal area of the substrate assembly 16 that surrounds the treatment device 22 and is non-overlapping with the treatment device 22, which is also attached to the substrate assembly 16, to provide maximum adhesion to the skin of the patient 100.

The substrate members 18a and 18b are preferably sized similarly and define the maximum extent of both the bandage 10 and the substrate assembly 16 in plan view. In accordance with one or more embodiments of the present invention, a pressure bandage 10 exerts a pressure P having a pressure component 190 and one or more pressure components 191. The pressure component 190 is the result of the force F1 and F2 and each pressure component 191 is the result of only the force F2.

The minimum size of the substrate assembly 16 is determined by the size of the adhesive area 20b needed for an adhesive 20a to create the force F2 to overcome the forces F1a and F1b of the pressure member and to adhere the bandage 10 to the skin with sufficient forces to overcome unintended removal of the bandage 10 from the skin. Thus, when the bandage 10 has been applied to the patient 100, at least the force F1c is exerted onto the treatment device 22, in turn, creating the pressure 190 onto at least the treatment area 114.

In accordance with one or more other embodiments of the present invention, the size of the substrate assembly 16 may be determined by the size of adhesive area 20b needed for the adhesive 20a to create the force F2 to overcome at least the forces F1a and F1b of the pressure member, to adhere the bandage 10 the skin of the patient with sufficient forces to overcome unintended removal of the bandage 10 from the skin, and, further to add to the pressure applied by the pressure member 14 to the treatment device. Thus, preferably, the adhesive placed in the adhesive area 20b exerts a force F2 onto the substrate assembly 16, or more specifically, to the pressure member 14 to prevent the pressure member from removing the bandage from the skin of the patient. Thus, when the bandage 10 has been applied to the patient 100, the force F1c and a portion of the force F2 is exerted onto the treatment device 22, in turn, creating the pressure 190 onto at least the treatment area 114.

The pressure member 14 may be disposed in the substrate assembly 16 by being embedded or sandwiched between the substrate members 18a and 18b and additionally may be secured as described below. However, the pressure member 14 may also be disposed or embedded solely within one of the substrate members or may be embedded such that a longitudinally-extending or laterally-extending portion of the pressure member is embedded solely in one substrate member. The other longitudinally-extending or laterally-extending portion of the pressure member is then embedded in the other substrate member or when three or more substrate members are present in one or more of the other substrate members.

In addition, the pressure member 14 may be joined to, joined with, disposed in, or disposed on, or embedded in the substrate using an adhesive, sonic welding, heating, stamping, or any other suitable means that aids in avoiding unintended movement of the pressure member 14 relative to the substrate assembly 16.

Regardless of how the pressure member 14 is disposed in the substrate assembly 16, the substrate assembly 16 comprises a marginal edge area 18c in plan view between a perimeter of the pressure member and a perimeter of the substrate assembly. The marginal edge area 18c also advantageously aids in keeping the pressure member 14 securely located relative to the substrate assembly 16.

The substrate members 18a and 18b may be secured to each other by using an adhesive, sonic welding, heating, stamping, or any other suitable means that aids in avoiding unintended movement of the substrate members relative to each other. Moreover, the perimeter and/or a perimeter margin of the substrate assembly 16 may have a finished and reduced thickness relative to other portions of the substrate assembly 16 by crimping, flattening, sonically welding, and/or stamping the perimeters of the substrate members 18a, 18b. This advantageously prevents the unintended separation of the substrate members from each other.

The treatment device 22 is joined to the substrate assembly 16 using an adhesive, sonic welding, heating, stamping, or any other suitable means that aids in avoiding unintended dislocation of the treatment device relative to the substrate assembly.

In accordance with one embodiment of the present invention, the treatment device 22 may comprise or consist of an absorbent pad made from cotton gauze or fabric, but the treatment device 22 may also comprise or consist of an absorbent material impregnated with one or more antibacterial agents or substances generally known in the art.

The treatment device 22 may also may comprise or consist of one or more scar reducing materials such as silicone formed into a pad.

The treatment device 22 may also comprise or consist of a combination pad wherein a skin proximal layer is an absorbent material joined to a skin distal layer made of one or more scar reducing materials. This advantageously immediately permits hemostasis and initiates a regimen of scar reduction.

In accordance with one or more embodiments of the present invention, the treatment device 22 for a wound may comprise an absorbent material and may have a thickness of approximately 220-500 microns at a center of the pad for maximum comfort and absorbency while marinating a clinically suitable pressure on the wound. The treatment device 22 may have a silicone pad for scar reduction and may achieve a pressure of 10 to 25 mm Hg, i.e., 10 to 25 Torr, of pressure under the pad for a clinically suitable pressure to reduce scarring.

In accordance with one or more embodiments of the present invention, the treatment device 22 may comprise one or more therapeutic agents beneficial to wound healing and/or scar reduction that may be disposed in or on the absorbent pad of the treatment device, but also packaged with bandage 10 in a kit. For example, therapeutic agents may be Vitamin E and/or one or more hemostatic and/or coagulative agents. Hemostatic and/or coagulative agents may comprise epinephrine, calcium alginate, calcium-loaded zeolite, cellulose, microfibrillar collagen, fibrinogen, glucosamine, thrombin, coagulation factors (e.g. II, VI, VII, X, XIII, VWF), procoagulants, antifibrinolytics (e.g. epsilon aminocaproic acid), and/or similar compounds.

A therapeutic agent may also be an antibiotic disposed in or on the treatment device, but also packaged with the bandage 10 in a kit. A therapeutic agent may be, but is not limited to, cephalosporins, polymyxin B sulfate, bacitracin, neomycin, polysporin), antiseptics (such as iodine solutions, silver sulfadiazine, chlorhexidine) and/or other treatments (e.g. botulism toxin, growth factors).

The bandage 10 preferably includes a pair of protective sheets disposed on the side proximal to the treatment device as are generally known in the art.

The bandage 10 may also be packaged in a sterile packaging that is easily removable by peeling two protecting sheets apart as is generally known in the art.

Since the bandage 10 generally follows the same curved contour as the pressure member 14 in the curved state 15a, the curved shape of the bandage, advantageously, permits nested packaging.

A plurality of the bandages 10 may be packaged to have treatment regimen starting with control of the wound using the bandages having treatment devices consisting of absorbent pads to bandages having treatment devices consisting of combination pads and ending with bandages having treatment devices having only scar reducing materials.

In accordance with one or more embodiments of the present invention, the bandage 10 may also be used for treatment of skin-related conditions such as skin injuries, including for example, incisions, acute or chronic wounds, ulcers, and venopuncture areas; preventing or reducing the incidence of wound infections, swelling and hematoma formation; treatment of skin irritation and sensitivity, skin paresthesia, allodynia, dermatitis, warts, rashes, acne, and psoriasis; management of arteriovenous malformations; treatment or improvement of wrinkles, scars, stretch marks or other skin irregularities; and/or delivering a drug to the skin or through the skin.

In accordance with one or more embodiments of the present invention, the bandage 10 further comprises, in any convenient location, one or more designs, logos, advertisements, treatment information, contact names and numbers, and/or marketing information.

In accordance with one or more embodiments of the present invention, the bandage 10, as for example, illustrated in FIGS. 2a-2f and 3a-3c, comprises a length 11a of approximately 50 mm to 190 mm and a width 11b of 22 mm to 100 mm. The bandage further comprises a thickness 11c in the range of 100 microns to at least 1 mm. Greater thicknesses may be possible depending on the thickness of the pressure member and generally vary between 1 mm to 3 mm.

Other bandages 10 may be suitably dimensioned in accordance with needs associated with a wound 110 or scarring 118.

FIG. 5a is a top plan view of a bandage in accordance with one or more embodiments of the present invention. FIG. 5b is a bottom plan view of the bandage of FIG. 5a. FIG. 5c is a longitudinal side view of the bandage of FIG. 5b.

In accordance with one or more embodiments of the present invention, a bandage 10a is constructed similarly to bandage 10 except that the substrate assembly 16 has been replaced with a substrate assembly 16a, which comprises a single substrate member 18a. The single substrate member, preferably, comprises one or more layers made of material 19b and at least one covering made of material 19a. However, preferably, two coverings made of material 19a sandwich the one or more layer made of material 19b. Therein, the pressure member 14 may be disposed within the single substrate member in a manner taught above.

The substrate member 18a may also consist of a single structural layer made of material 19a. Then, the pressure member 14 is joined to an underside of the substrate member 18a, i.e., the substrate assembly 16, using an adhesive, sonic welding, heating, stamping, or any other suitable means that aids in avoiding unintended removal of the pressure member.

The treatment device 22 is then secured directly to the pressure member by an adhesive, sonic welding, heating, stamping, or any other suitable means that aids in avoiding unintended movement of the treatment device relative to pressure member.

Thus, the adhesive area 20b is disposed directly on the underside of the substrate member 18a and may also be disposed at least partially on an area of the pressure member 14 that is not covered by the treatment device 22.

Advantageously, the bandage 10a provides a simple and cost effective construction.

FIG. 6a is a top plan view of a bandage in accordance with one or more embodiments of the present invention. FIG. 6b is a bottom plan view of the bandage of FIG. 6a. FIG. 6c is a longitudinal side view of the bandage of FIG. 6b.

In accordance with one or more embodiments of the present invention, a bandage 10b is constructed similarly to bandage 10 except that the pressure member 14 is secured to the substrate assembly 16 on a side opposite to a side to which the treatment device 22 are secured.

Therein, the pressure member 14 is secured to a first side 16b of the substrate assembly 16. The substrate assembly 16 may be any substrate assembly as taught above, but, preferably, the substrate assembly 16 comprises a single substrate member 18a that, in turn, consists of a single structural layer made of material 19a. The pressure member is secured to the first side by an adhesive, sonic welding, heating, stamping, or any other suitable means that aids in avoiding unintended movement of the pressure member relative to the substrate assembly.

The treatment device 22 is secured directly to a second side 16c of the substrate assembly 16 by an adhesive, sonic welding, heating, stamping, or any other suitable means that aids in avoiding unintended movement of the treatment device relative to pressure member.

The adhesive area 20b is disposed directly on the underside of the substrate member 18a, i.e., substrate assembly 16, in an area not covered by the treatment device 22.

FIG. 7a is a plan view of a pressure member in accordance with one or more embodiments of the present invention. FIG. 7b is a cross-sectional view of the pressure member of FIG. 7a. FIG. 7c is a first alternate cross-sectional view of the pressure member of FIG. 7a. FIG. 7d is a second alternate cross-sectional view of the pressure member of FIG. 7a.

Therein, a pressure member 202 is substantially identical to the pressure member 14 and may be used in any of the bandages taught above. However, the pressure member 202 comprises end portions 202a, which correspond to end portions 14a, that are wider laterally than central portion 202b, which corresponds to the central portion 14b. Advantageously, the configuration permits increasing the forces F1a and F1b and placing the force F1c over a smaller surface area. Since pressure is the force per unit area, the force F1c will thus be able to increase pressure the treatment device by concentrating the pressure over a smaller area.

In addition or in the alternative, the pressure member 202 comprises ridges 202c that may be squared, rounded, or peaked and aid in increasing the amount of pre-tensioning possible and increasing the force F1c.

FIG. 7e is a plan view of a pressure member in accordance with one or more embodiments of the present invention. Therein, a pressure member 204 is substantially identical to pressure member 14 and may be used in any of the bandages taught above. However, pressure member 204 comprises end portions 204a, which correspond to end portions 14a, that are wider laterally than the central portion 204b, which corresponds to central portion 14b. End portions 204a include one or more indentations 204c, which permits the pressure member 204 to be more flexible at the end portions and be fitted in unusual anatomical situations to a patient.

FIG. 7f is a plan view of a pressure member in accordance with one or more embodiments of the present invention. Therein, a pressure member 206 is substantially identical to pressure member 14 and may be used in any of the bandages taught above. However, the pressure member 206 comprises end portions 206a and central portions 206b, all of which have been widened, but have portions that connect them and that are not as wide as the portions 206a and 206b.

FIG. 8a is a plan view of a pressure member in accordance with one or more embodiments of the present invention. FIG. 8b is a longitudinal cross-sectional view of the pressure member of FIG. 8a. FIG. 8c is an alternate longitudinal cross-sectional view of the pressure member of FIG. 8a.

Therein, a pressure member 208 is substantially identical to pressure member 14 and may be used in any of the bandages taught above. However, the pressure member 208 comprises end portions 208a, which correspond to end portions 14a, that are wider laterally than central portion 208b, which corresponds to central portion 14b. End members 208a may also have a greater thickness than central portion 208b. The difference in thickness may be distributed relative to one or both sides of the central portion. Advantageously, the configuration permits increasing forces F1a and F1b and placing force F1c over a smaller surface area. Since pressure is the force per unit area, force F1c will thus be able to increase pressure the treatment device by concentrating the pressure over a smaller area.

FIG. 9a is a plan view of a pressure member in accordance with one or more embodiments of the present invention. FIG. 9b is a plan view of a pressure member in accordance with one or more embodiments of the present invention. FIG. 9c is a longitudinal cross-sectional view of the pressure member of FIG. 9b.

Therein, a pressure member 210 is substantially identical to pressure member 14 and may be used in any of the bandages taught above. However, the pressure member 210 comprises a plurality of disconnected strips 210a that may be arranged in one or more planes. This permits the pressure member to be more flexible.

The pressure member 210 may also comprise a plurality of disconnected strips 210a and 210b that may be arranged in one or more planes and/or may be stacked on top of each other.

The strips 210b are preferably, but not necessarily, arranged at the end portions of the pressure member 210 causing the pressure member to have a greater thickness at one or more end portions than a central portion. This permits the pressure member to be more flexible as well as increasing the forces F1a and F1b and placing the force F1c over a smaller surface area. Since pressure is the force per unit area, the force F1c will thus be able to increase pressure on the treatment device.

FIGS. 10a-10c and 11a-11c are, respectively, plan, side, and side on skin views of a bandage in accordance with one or more embodiments of the present invention. Therein, a bandage 10d or 10e comprises a plurality of pressure members 14 that are arranged to overlap and/or have a woven configuration. This permits the bandages 10d and 10e to conform in not flat situations, such as the antecubital fossa.

FIG. 12a is a longitudinal side view of a pre-stressed pressure device is configured as a stress guard prior to being applied to a patient in accordance with one or more embodiments of the present invention. FIG. 12b is a longitudinal side view of the stress guard of FIG. 12a applied to a patient when initially applied to an open incision site. FIG. 12c is a longitudinal side view of the stress guard of FIG. 12a after being stressed. FIG. 12d is a first detail view of the stress guard of FIG. 12a. FIG. 12e is a second detail of the stress guard of FIG. 12a.

A pre-stressed pressure device is configured as a stress guard 40. Returning to FIG. 1a, the stress guard 40 is preferably used to treat the wound 110, which may be a wound caused by a surgical incision, and prevent scarring associated with the wound. Therein, the wound 110 typically will be sutured, and, thus, the wound area 112 is nil and the treatment area 114 extends to encompass the area scarred by scarring 118. To treat the wound 110 and prevent likely scarring 118, a pressure 192, i.e., a stress 192 is applied by a treatment device on at least a portion of the treatment area 114 using the stress guard 40.

Therein, the stress guard 40 is preferably pre-stressed with a curve designed to maximize inward force while applied to the skin with preferably a peelable adhesive disposed on end portions of the stress guard but not on the central portion. The stress guard can be manually strained and applied flat to the skin. The stress at the wound site may be reduced to the levels below that experienced by normal skin.

In accordance with one or more embodiments of the present invention, the stress guard 40 comprises a pressure member 44, which exerts pressure 192 on the wound 110 to close the wound area 112, if open, and/or relieve stress in the wound area 112, and an adhesive 46a applied in one or more adhesive areas 46b.

The pressure member 44 comprises one or more layers of one or more pressure materials. A pressure material may be any suitable material that is elastic and capable of holding an initial non-flat shape, preferably a curved shape. However, preferably, the pressure material is a polymer material. More preferably, the pressure material is selected from the group of polyvinyl chloride (PVC), acrylonitrile butadiene styrene (ABS); nylon polymers including polyamide 6, polyamide 66, homopolymers, and co-polymers; polyester resin; low-density polyethylene terephthalate (PET); low-density polyethylene, high-density polystyrene; high-density polyethylene; and rubberized and/or plasticized PVC.

The pressure member 44 comprises, but not necessarily, a generally rectangular shape in plan view having end portions 44a (each defined as being generally, but not necessarily, the one-third end area in side view of the pressure member) spaced distal from a central portion 44b (defined as being generally, but not necessarily, the center one third area in side view of the pressure member) and has a thickness 44c. The thickness 44c is preferably sufficient to prevent the longitudinal edges of the pressure member 44 from curling inwards towards a longitudinal centerline of the pressure member. That is, the thickness 44c is chosen such that the pressure member remains rigid in a cross-section perpendicular to the longitudinal centerline of the pressure member.

Therein, the thickness 44c may be varied as needed for the specific embodiment of the stress guard 40 and may be non-uniform and variable in thickness across the width and/or along the length of the pressure member 44. The thickness preferably also provides stress guard with sufficient load carrying capacity to achieve the desired pressure 192. The thickness 44c of the pressure member 44 may be tapered near the edges for added comfort and/or safety of use.

The pressure member 44 normally has a curved shape in at least part of the central portion 44b while the end portions 44a are straight. In other words, the pressure member 44 has a normally curved state 45a, i.e., first state. This state occurs prior to the stress guard 40 being applied to the skin of the user.

The curved shape in at least part of the central portion 44b may be achieved by casting, extruding, and/or forming central portion to be curved. Therein, the central portion 44b may have any suitable curve while the end portions 44a are straight.

The curved shape may also be made by pre-tensioning the pressure member in a pre-stressed area (not shown), such as being heat-treating. Therein, the pre-stressed area is preferably disposed in the central portion 14b. In the pre-stressed area, the pressure member has been stressed increasing a compression side, moving the neutral axis in the pre-stressed area, and causing a tension side to be reduced.

In the curved state 45a, the pressure member 44 is curved in the pre-stressed area, while the end portions 44a are straight. Therein, the end portions 44a are preferably, but not necessarily, equidistant from the central portion 44b in lateral and offset directions and are curved in the same direction. When the pressure member 44 is in the curved state 45a, the stress guard 40 generally follows the same curved contour as the pressure member 44 and also is in the curved state 45a.

In accordance with one or more embodiments of the present invention, one or more hinges 43 define the boundary between the central portion 44b and respective end portions 44a. Therein, the hinge 43 may be a plastic hinge or hinge having a groove or a channel 43a. The groove or channel 43a may be formed to be a V opening wherein each leg of the V has equal length, or has an unequal length.

Preferably, the adhesive 46a may be one or more suitable pressure-sensitive adhesives as is known in the art for adhesive bandages. Due to their excellent adhesion strength, usability, costs, and/or length of use, the adhesive 46a is preferably selected from the group of acrylic, silicone, butyl rubber, nitrile, styrene block copolymers (SBC), ethylene-vinyl acetate (EVA), or a combination thereof. In addition or in the alternative, the adhesive 46a may be a polyacrylate-based, polyisobutylene-based, and/or silicone-based pressure-sensitive adhesive; or a synthetic rubber, acrylic, hydrocolloid, or a like compound adhesive. In addition or in the alternative, adhesive 46a may also be a light-curable or heat-curable adhesive.

Preferably, regardless of type, adhesive 46a comprises a T-peel release force of in the range of 0.45 N/cm to at least 19 N/cm. Therein, the T-peel release force and blunt probe tack force of pressure-sensitive adhesives is in accordance with ASTM D1876 and ASTM D2979 or other appropriate methods.

The adhesive 46a is applied in the adhesive area 46b, which is preferably a portion of or all of end portions 44a. The adhesive 46a is preferably not applied in the central portion 44b.

The stress guard 40 is applied to the patient 100, for example, by straining it manually and then using the adhesive 46a to secure it to skin of the patient. Therein, the pressure member 44 will be in a non-curved, substantially the non-curved state 45b, i.e., second state. When the pressure member 44 is in substantially non-curved state 45b, the stress guard 40 follows the same contour as the pressure member 44 and also is in substantially the non-curved state 45b. Substantially non-curved state 45b may be a flat state or contour, and/or may be one where the pressure member, i.e., stress guard, follows the contour of the skin.

In either curved state 45a or substantially the non-curved state 45b, the pressure member 44 has the forces F3 and F4, which combine as pressure 192 and are directed toward each other to pull the wound 110 closed. That is, when the pressure member 44 is curved, the forces F3 and F4 pull toward each other closing the wound 110 or keeping the marginal edges of the wound closed.

Preferably, a stress guard 40 is selected so that it is sufficiently sized, for example, by laying in a substantially non-curved state 45b when applied to a wound, as shown in FIG. 12b, and the wound's edges are being pulled toward each other to close the wound area 112, if open, and/or relieve stress in the wound area 112. As the wound heals, the wound area 112 becomes nil and the stress guard changes to a substantially curved state 45a.

Advantageously, the pressure material may be pre-stressed to a predetermined amount, and thus, the amount of curvature may be selectively predetermined to the pressure member 44. In turn, by varying the curvature, the central portion 44b can be predetermined to exert specific forces F3 and F4 on the wound 110. In addition or in the alternative, the shape and/or the thickness 44c of the pressure member may be selected, as taught further herein, to provide further predetermined refinement of forces F3 and F4. Forces F3 and F4 are transferred as pressures to the patient via the treatment device, since pressure is force per unit area.

Therein, increasing forces F3 and F4 will yield an increase in pressure applied to at least the treatment area 114 via the treatment device.

The pressure member 44 may have a thickness of 100 microns to at least 2 mm, but preferably with a range of about 220 microns to about 500 microns, or more preferably 300 microns to 400 microns. The pressure member 44 preferably has a length of approximately 10 mm to 190 mm, i.e., 1 cm to 19 cm, and/or a width of 8 mm to 100 mm, i.e., 0.8 cm to 10 cm.

In accordance with one or more embodiments of the present invention, a kit for treating the wound 110 of the patient 100 comprises two different types pre-stressed pressure devices, i.e., the pressure bandage 10 and the stress guard 40, used at different times during the treatment for effective wound healing and to reduce the possibility of scarring. The pressure bandage 10 is indicated for use during the acute and late wound phases. These phases are immediately after the occurrence of the wound and up to 2 weeks after the occurrence of the wound. To treat the wound during the intermediate phase, between 2 and 12 weeks, the stress guard 40 is indicated. Therein, the system offers an ultimate solution to the skin wound treatment and scar tissue relief.

Figure 13:
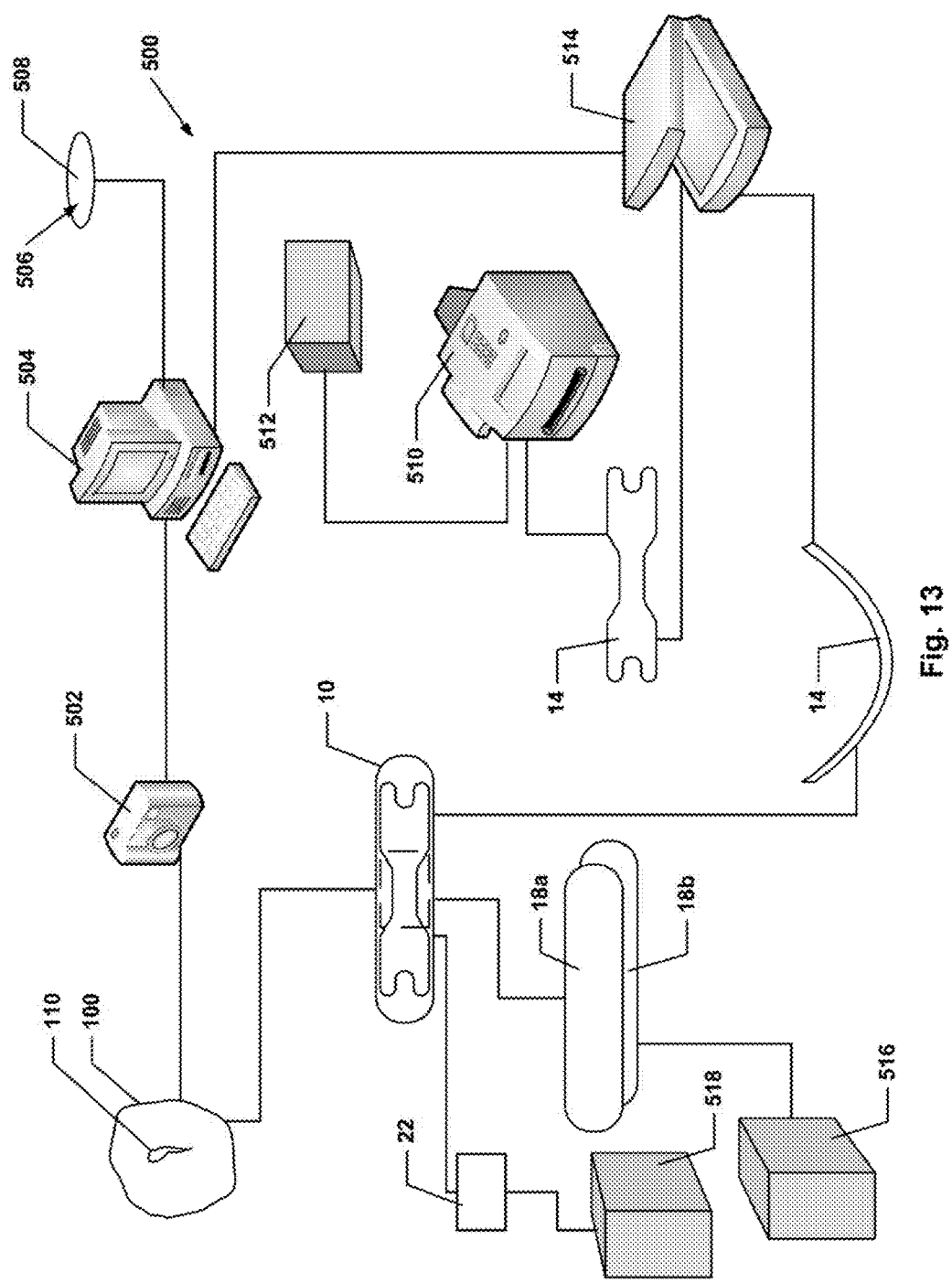
FIG. 13 is a diagram illustrating a treatment system for making a pre-stressed pressure device for treating a wound and/or reducing scarring in accordance with one or more embodiments of the present invention.

FIG. 13 is a diagram illustrating a treatment system for making a pre-stressed pressure device for treating a wound and/or reducing scarring in accordance with one or more embodiments of the present invention. Therein, the treatment system 500 for treating a wound and/or reducing scarring comprises an imaging device 502, a computing device 504 executing a computer-readable software 506 stored on a non-transitory computer readable media 508, a 3D printer 510, a supply 512 of pressure material, a heating device 514, a supply 516 of substrate members 18a and 18b, and a supply 518 of treatment device 22.

Therein, when a patient 100 presents with a wound 110 or with scarring, a user of the system, who preferably, but not necessarily a qualified medical professional, uses imaging device 502, such as a digital camera, smartphone camera, ultraviolet imaging apparatus, to take an image of the wound or scarring and/or the contours of the area surrounding the wound or scarring. Using a network or a storage device, the image is then transferred to a computing device 504 such as a computer, mainframe device, tablet computer, smartphone, or other device. The network herein may be any kind of network including a cellular, wireless, Wi-Fi, LAN, Ethernet, internet, private, public, or a combination thereof.

In accordance with one or more embodiments of the present invention, the image is utilized by the user to define treatment area 114. Software 506 stored on a non-transitory computer readable media 508, such as CD-ROM or DVD, uses the defined treatment and/or contours of the surrounding area to design the pressure member 14, including the shape of the end portions 14a, the central portion 14b, the thickness 14c for any portion and any variations therein as taught above, and transmits that information, preferably over a network, to the 3D printer 510. The software then also calculates the amount of pre-tensioning required and transmits that information, preferably over a network, to heating device 514.

Therein, the 3D printer 510 may be any suitable additive manufacturing printer. The printer 510, using supply 512 of the pressure material, manufactures the pressure member 14 according to the information sent by computing device. The same user or another user then places the pressure member in the heating device 514.

The heating device 514 may be any kind of suitable device that imparts energy into the pressure member 14. Thus, heating device 514 may be a microwave, a radiant heater, a sonic welding device, or a combination thereof. Using the information sent by the computing device, the heating device 514 heats the pressure device 14 in the pre-stressed area 14d to impart the pre-tensioning. In order to prevent unintended heating, a protective layer may be printed on areas of the pressure device other than the pre-stressed area 14d.

In addition or in the alternative, the pressure member 14 may also be made to be curved in the printer 512 and heating with the heating device 514 may not be necessary.

After the pre-tensioning has been imparted in the pressure member 14, it is joined to one or more substrate members 18a and 18b that are provided via a supply 516 and a treatment device 22 from the supply 518. If necessary, the substrate members 18a and 18b and the treatment device 22 may be sized according to sizing information provided by the computing device 504 to produce a pre-stressed pressure device configured, for example, as the bandage 10 that may be applied to the patient. Similarly, the stress guard 40 may be produced by the treatment system 500 by itself and/or in conjunction with the pressure bandage 10.

While the invention has been described in conjunction with specific embodiments, it is to be understood that many alternatives, modifications, and variations will be apparent to those skilled in the art in light of the foregoing description.

What is claimed is:

1. A pressure device for treating a wound or reducing scarring of a skin of a patient, the pressure device comprising:
   a substrate assembly having a first surface side and a second surface side, as well as first and second end portions;
   a pressure member having a curved state and a non-curved state, the pressure member having an inner surface and an outer surface, the pressure member also comprising a central portion and first and second end portions,
   the central portion having a convex curved shape along the outer surface of the pressure member when the pressure device is not adhered to the skin of the patient, and the pressure member being connected to the second surface side of the substrate assembly;
   a treatment device connected to the outer surface of the pressure member, wherein the first and second end portions of the pressure member extend beyond ends of the treatment device; and
   an adhesive located on the first and second end portions of the substrate assembly and the first and second end portions of the pressure member for applying the pressure member to the skin of the patient;
   wherein when the adhesive secures the skin of the patient to the first and second end portions of the substrate assembly and the first and second end portions of the pressure member, and the pressure member is in the non-curved state, the pressure member exerts end forces directing the first and second end portions of the pressure member away from the skin of the patient and a central force directing the central portion of the pressure member towards the skin of the patient.

2. The pressure device of claim 1, wherein the pressure member exerts a pressure ranging from 10-25 mm Hg to the wound when secured to the wound in the non-curved state.

3. The pressure device of claim 1, wherein the substrate assembly comprises a woven cloth, cotton, artificial and/or natural fibers, artificial and/or natural gel materials, natural or artificial foamed rubber, or a combination thereof.

4. The pressure device of claim 1, wherein the treatment device comprises a silicone pad, a gauze, an anti-bacterial agent treated pad, a coagulant agent treated pad, a hemostatic agent treated pad, a vitamin E treated pad, an antibiotic treated pad, an antiseptic treated pad, a botulism toxin treated pad, or a growth factors treated pad.

* * * * *